US008826723B2

(12) United States Patent
Henry (10) Patent No.: US 8,826,723 B2
(45) Date of Patent: Sep. 9, 2014

(54) ASSESSING ODORS (75) Inventor: Christopher G. Henry, Stuttgart, AR (US)

(73) Assignee: NUtech Ventures, Lincoln, NE (US)

(*) Notice: Subject to any disclaimer, the term of this patent is extended or adjusted under 35 U.S.C. 154(b) by 340 days.

(21) Appl. No.: 13/421,048

(22) Filed: Mar. 15, 2012

(65) Prior Publication Data

US 2013/0239657 A1 Sep. 19, 2013

(51) Int. Cl.
*G01N 33/497* (2006.01)
*G01N 33/00* (2006.01)
*G01N 1/22* (2006.01)

(52) U.S. Cl.
CPC .......... *G01N 33/0011* (2013.01); *G01N 1/2273* (2013.01)
USPC ......................................................... 73/23.34

(58) Field of Classification Search
CPC ............ G01N 33/0004; G01N 1/2273; G01N 33/0011
USPC ......................................................... 73/23.34
See application file for complete search history.

(56) References Cited

U.S. PATENT DOCUMENTS

| | | | | | |
|---|---|---|---|---|---|
| 2,136,844 | A | * | 11/1938 | Fair et al. ...................... | 73/23.34 |
| 3,902,851 | A | * | 9/1975 | Dravnieks ..................... | 73/23.34 |
| 5,313,821 | A | * | 5/1994 | Bett et al. ...................... | 73/23.34 |
| 6,018,984 | A | * | 2/2000 | McGinley et al. ............ | 73/23.34 |
| 6,338,715 | B1 | * | 1/2002 | Hayes et al. ................... | 600/303 |
| 6,595,037 | B2 | * | 7/2003 | McGinley ..................... | 73/23.34 |
| 6,694,759 | B1 | * | 2/2004 | Bash et al. ..................... | 62/180 |
| 7,145,086 | B2 | * | 12/2006 | Iiduka et al. .................. | 177/180 |
| 7,856,863 | B2 | * | 12/2010 | Kvasnik et al. ............... | 73/23.2 |
| 8,429,950 | B2 | * | 4/2013 | Wright .......................... | 73/23.34 |
| 2009/0038555 | A1 | * | 2/2009 | Reese ............................ | 119/174 |

OTHER PUBLICATIONS

Stowell et al., "Association of Odor-Measures with Annoyance: Results of an Odor-Moniotiring Field Study", Nebraska Swine Reports, University of Nebraska—Lincoln, Jan. 1, 2008.*
Henry; Development of the Mask Scentometer, a Comparison of Ambient Odor Assessment Methods, and their Application in Ground Truthing Atmospheric Dispersion Models; Biological Systems Engineering—Dissertations, Theses, and Student Research; 2009; p. 203.
St. Croix Sensory, Inc; Odor Sensitivity Test; 2005; p. 15.
St. Croix Sensory, Inc. ; The Nasal Ranger Field Olfactometer—Operation Manual Version 6.2; 2008; p. 24.

* cited by examiner

*Primary Examiner* — David A Rogers
(74) *Attorney, Agent, or Firm* — Fish & Richardson P.C.

(57) ABSTRACT

In some aspects, olfactory devices include a housing having a first inlet and a second inlet, an ambient air inlet cartridge defining a channel in fluid communication with the first inlet, and a position sensor. The ambient air inlet cartridge includes a first member defining a first orifice, and a second member moveable relative to the first member, the second member defining a second orifice, where a degree of overlap between the first orifice and the second orifice controls a flow capacity of the channel. The position sensor signals the degree of overlap between the first orifice and the second orifice.

18 Claims, 8 Drawing Sheets

ASSESSING ODORS

TECHNICAL FIELD

This invention relates to systems and methods for assessing odors.

BACKGROUND

Field olfactometry is the use of a technique or device to measure odor in ambient air by a single individual. Field olfactometry can be used to detect levels of odor in ambient air near industrial, agricultural, and municipal operation sites, such as facilities for wastewater treatment, landfills, composting, and manufacturing. Many governmental bodies require that the level of odor in the air surrounding such sites conform to various regulatory guidelines to reduce the impact on the general public.

SUMMARY

Field olfactometry works generally by measuring the quantity of odor in ambient air by dynamically mixing filtered, clean non-odorous air with ambient, odorous air. The odorous ambient air is added to the filtered, clean air in increasing quantities by changing the ratio of air volumes until the odor is detected by a human's senses. The point at which the odor is first detected is called the dilution to threshold ratio (D/T), which means that an odor has been diluted to the threshold where a human's olfactory nerves detect the odor in the ambient air. Controllably varying the dilution to threshold ratio through a continuous range of dilutions can provide a highly precise quantification of the levels of present at a site being assessed.

In an aspect, olfactory devices include a housing having a first inlet and a second inlet, an ambient air inlet cartridge defining a channel in fluid communication with the first inlet, and a position sensor. The ambient air inlet cartridge includes a first member defining a first orifice, and a second member moveable relative to the first member, the second member defining a second orifice, where a degree of overlap between the first orifice and the second orifice controls a flow capacity of the channel. The position sensor signals the degree of overlap between the first orifice and the second orifice.

In an aspect, olfactory devices include a housing having a first inlet and a second inlet, and an ambient air inlet cartridge defining a channel in fluid communication with the first inlet. The ambient air inlet cartridge includes a first member defining a first orifice, and a second member moveable relative to the first member, the second member defining a second orifice where a degree of overlap between the first orifice and the second orifice controls a flow capacity of the channel, the second member being movable relative to the first member between a first terminal end position, where the first and second orifices are offset from one another, and a second end position, where the first and second orifices are completely aligned. As the second member moves between the first terminal end position and the second terminal end position, the degree of overlap between the first orifice and the second orifice increases over a continuous range.

In an aspect, methods of assessing odor include withdrawing an amount of filtered air into a housing, withdrawing an amount of ambient air into the housing to form a mixture, where the amount of ambient air is less than the amount of filtered air, determining the presence of an odor in the mixture, in response to determining that no odor is present, increasing the amount of ambient air withdrawn into the housing, the amount of ambient air being increased through a continuous range, and when an odor is detected, determining a ratio of the amount of filtered air to the amount of ambient air being withdrawn into the housing.

Embodiments can include one or more of the following features.

In some embodiments, the position sensor includes a visual scale formed on the first member or the second member.

In some embodiments, the position sensor includes a potentiometer to detect a position of the second member relative to the first member and output a position signal. In some cases, the potentiometer includes a detection membrane secured to the first member and a position indicator secured to the second member. In some cases, the olfactory device also includes a controller to receive the position signal to determine a characteristic relating to the position of the second member relative to the first member. In some cases, the olfactory device also includes a display unit to display the characteristic. In some cases, the characteristic is an approximated air flow ratio of an amount of air entering the housing through the second inlet to an amount of air entering the housing through the first inlet.

In some embodiments, the second orifice overlaps the first orifice to define a compounding air flow passage that increases over a continuous range as the second member moves between a first position and a second position. In some cases, when the second member is in the first position, an amount of air that can enter the housing through the ambient air inlet cartridge is greater than the amount of air that can enter the housing through the ambient air inlet cartridge when the second member is in the second position. In some cases, when the second member is in the second position, the first orifice is covered by the second member and the second member limits air flow from entering the housing through the ambient air inlet cartridge.

In some embodiments, the second member is a disk and the disk is rotatable relative to the first member.

In some embodiments, the first and second orifices have the same general shape and size.

In some embodiments, the second orifices has a first end having a first width and a second end having a second width, the second width being greater than the first end.

In some embodiments, the housing includes a face mask.

In some embodiments, the outlet is sized to be temporarily secured around a human nasal area.

In some embodiments, determining the ratio includes reading the ratio from a display unit.

In some embodiments, determining the ratio includes detecting a relative position of two orifices that move relative to one another to form a compounding air flow passage to allow the ambient air to enter the housing. In some cases, the compounding air flow passage changes in size along a continuous range.

Embodiments can have one or more of the following advantages.

The described systems and methods can be used to precisely quantify levels of odor present in ambient air by providing an ambient air inlet opening that can smoothly and continuously change in size to allow a continuous range of ratios of filtered air to ambient air.

The systems and methods described can enable a user to view an instantaneous dilution ratio to threshold as the user adjusts the olfactometer by including a display unit that provides the dilution to threshold ratio at a given time.

The details of one or more embodiments of the systems and methods are set forth in the accompanying drawings and the description below. Other aspects, features, and advantages of

DETAILED DESCRIPTION

Olfactory devices that mix filtered, clean air (i.e., air without an odor) with ambient, odorous air can be used to quantify a level of odor in the ambient air. The olfactory devices can vary a ratio of clean, filtered air to ambient, odorous air being administered to a person (e.g., a tester) to determine a dilution to threshold ratio (D/T) at which a human subject begins to detect the odor. Using an adjustable orifice formed by two orifices that are movable relative to one another to introduce the ambient air to enter an inhalation device (e.g., a gas mask) allows operators to assess odors throughout a continuous range of dilution to threshold ratios.

Scentometers can control the ratio of filtered to ambient air by controlling the size of the filtered air inlet and/or the ambient air inlet through which air enters the scentometer. The clean air cartridge typically has a fixed inlet size and the ambient air cartridge has a variable inlet size. Some scentometers have clean air cartridges with variable inlet sizes and/or ambient air cartridges with a fixed inlet size. The variable-sized inlets can be provided by two structural members (e.g., flat plates or disks) which each have apertures through which air can flow. The two structural members are movable relative to each other. The relative movement of the structural members adjusts the relative position of their apertures and controls the cross-sectional area of the portion of the flow path of air entering the device through the variable-sized inlet. Controlling the cross-sectional area controls the amount of air flowing through the variable-sized inlet. Thus, the ambient air dilution cartridge can allow a user to adjust the amount of unfiltered air that enters the mask.

Figure 1:
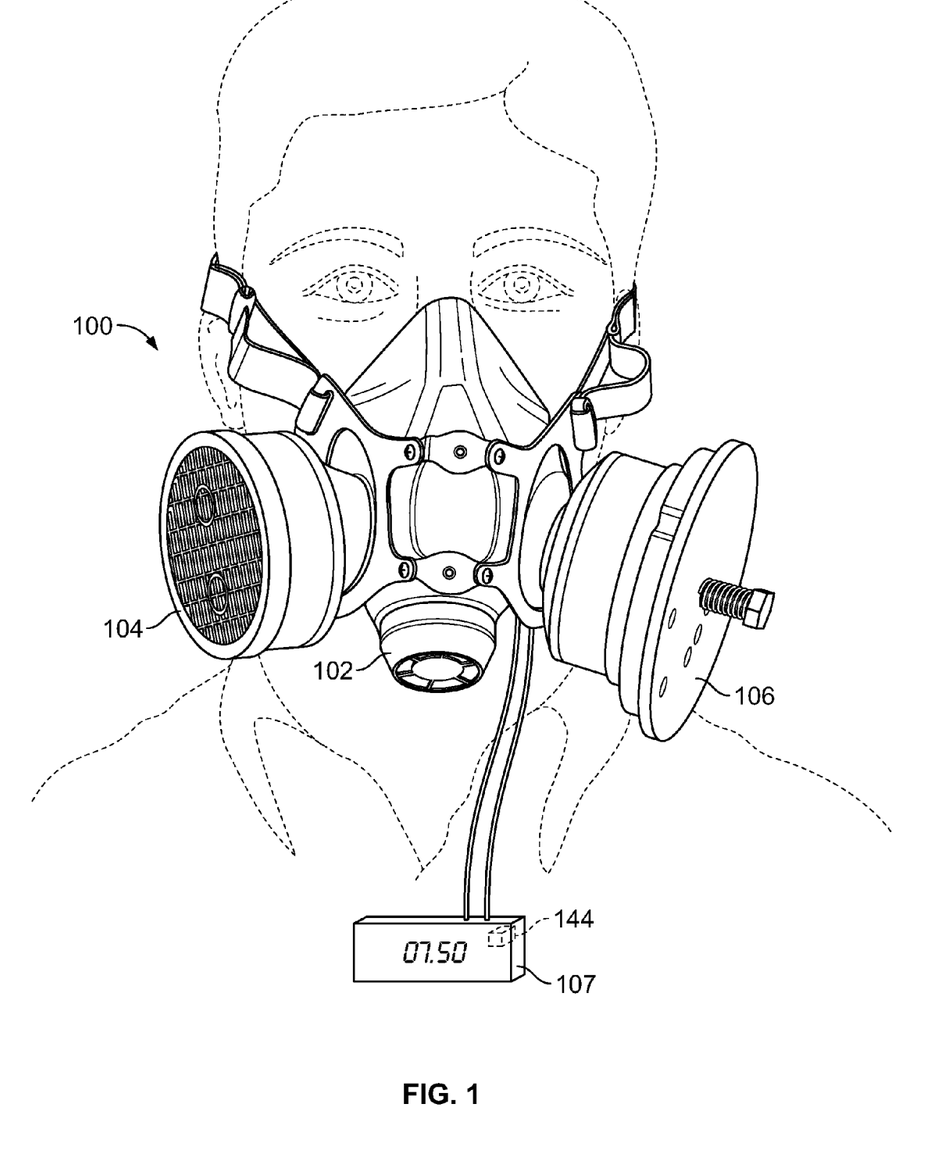
FIG. 1 is a perspective view of a mask scentometer.

Referring to FIG. 1, a scentometer (e.g., a mask scentometer) 100 includes a face mask 102, a clean air inlet cartridge 104, an ambient air dilution cartridge 106, and a display unit 107 (e.g., a digital display, a dial indicator, or similar device). The clean air inlet cartridge 104 and the ambient air dilution cartridge 106 are arranged on holes on opposite sides of the face mask 102 to allow both filtered and ambient air to flow into and mix within the face mask 102. The face mask 102 can be made from any of various suitable types of commercially available gas masks or face masks that cover the nose and mouth and can be secured to the face of the user (e.g., with straps). Commercially available masks having two odor reducing charcoal filters (e.g., one filter on each side of the mask) can be modified by removing and replacing one of the odor reducing charcoal filters with an ambient air dilution cartridge 106.

The clean air inlet cartridge 104 includes an odor reducing filter (e.g., a charcoal filter) that removes odors from the ambient air entering the mask 102 through the clean air inlet cartridge 104. Any of various suitable odor reducing filters can be used. As discussed above, commercially available odor reducing gas masks having activated charcoal filters can be retrofit by replacing one of the filters with the ambient air dilution cartridge 106.

Referring to FIG. 2A-2E, the ambient air dilution cartridge 106 includes a first structural member that is fixed in place and a second structural member that is movable relative to the first structural member. In the exemplary ambient air dilution cartridge 106, the first structural member is a fixed disk 108 and the second structural member is a pivoting disk 110 that pivots relative to the fixed disk 108. Some cartridges with variable-sized inlets have other configurations. For example, some ambient air dilution cartridges include rectangular plates that are laterally slidable relative to each other rather than disks which a rotatable relative to each other.

The fixed disk 108 and the pivoting disk 110 each include an orifice 109, 111 formed respectively extending through the disks 108, 110 to permit ambient air to flow into the mask 102. The pivoting disk 110 pivots relative to fixed disk 108 to vary the size of an air flow opening 113 (shown cross hatched for clarity in FIGS. 2A, 2D, and 2E) formed by the overlapping orifices 109, 111. In the example shown, as the pivoting disk 110 rotates counter-clockwise with respect to the fixed disk 108, the air flow opening 113 gets larger as the orifices 109, 111 align with each other.

The orifices 109, 111 have substantially the same shape. The pivoting disk 110 is moveable from a first position in which the two orifices 109, 111 align with one another (see FIG. 2E) to a second position in which the two orifices 109, 111 are offset from each other (see FIG. 2C). Each orifice increases in width as it extends circumferentially around each disk 108, 110. Each orifice 109, 111 has a first end 109A, 111A having a small width and smoothly extends into a second end 109B, 111B having a width that is wider than the first end 109A, 111A. Relative movement of the disks initially provides a very small opening 113 as a user begins to align the orifices 109, 111. The size of the opening 113 can be increased in a slow and controlled manner through a continuous range of sizes. In the illustrated device, the orifices 109, 111 are in the shape of a French curve. The orifices 109, 111 are formed along approximately 50% of the disks to provide a large adjusting range of the pivoting disk 110 relative to the fixed disk 108. In some embodiments, the orifices are different shapes. For example, some devices include rectangular plates having triangular orifices extending through the plates. As discussed below, the disks 108, 110 can include additional features or recesses.

Figure 2A:
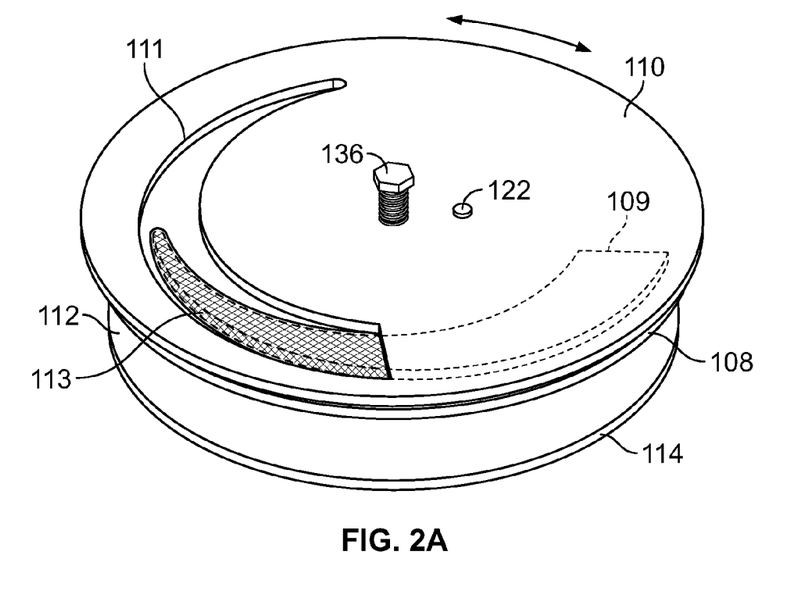
FIG. 2A is a perspective view of an ambient air dilution cartridge of the mask scentometer of FIG. 1.
Figure 2B:
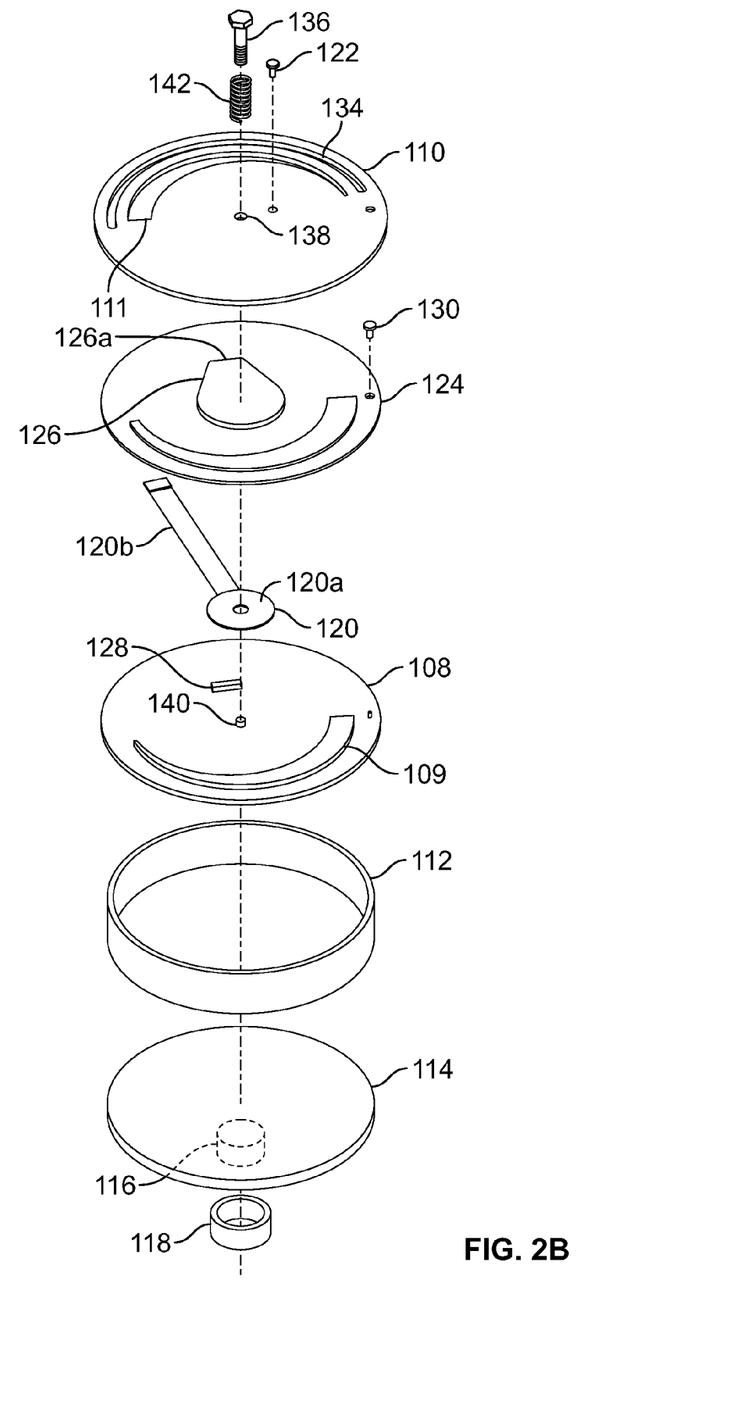
FIG. 2B is an exploded view of the ambient air dilution cartridge of the mask scentometer of FIG. 1.
Figures 2C, 2D, 2E:
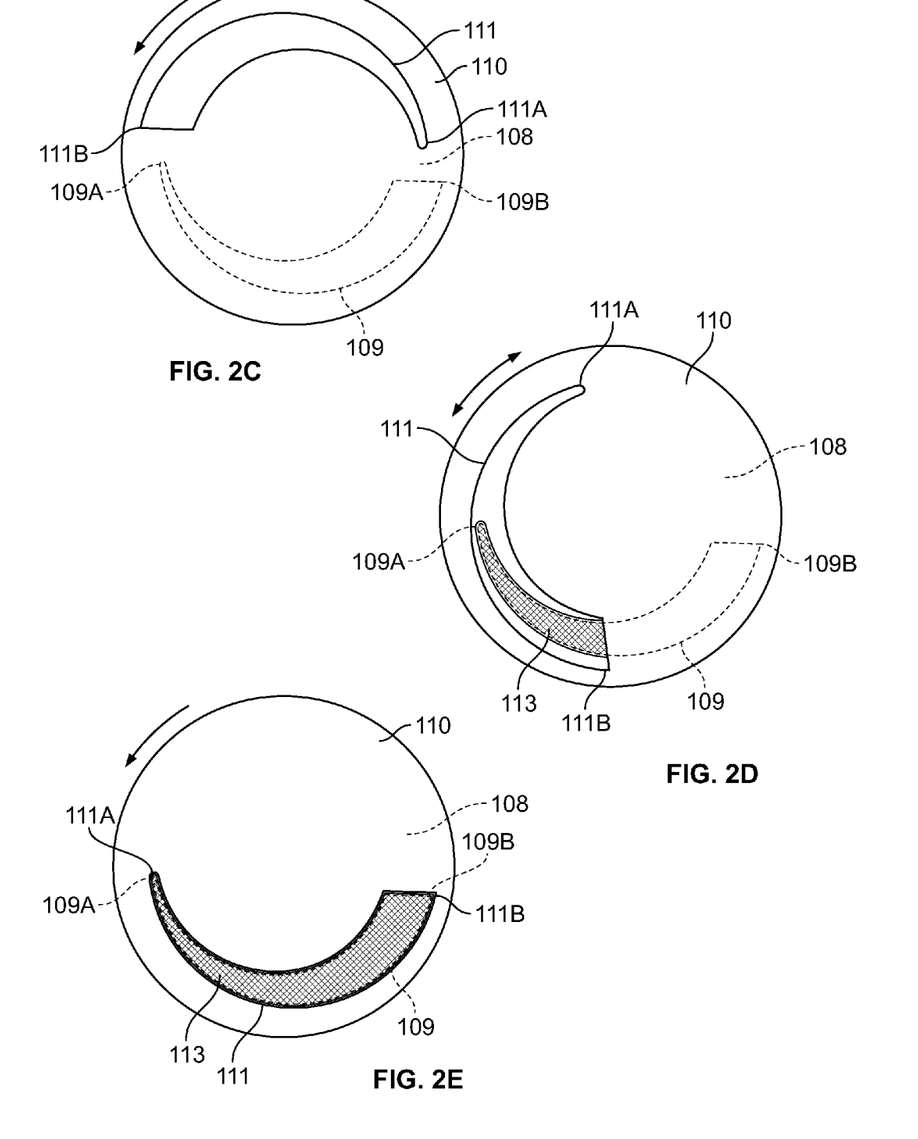
FIGS. 2C-2E are top views of a pivoting disk rotating on a fixed disk to create an ambient air opening for the mask scentometer of FIG. 1.

The fixed plate 108 is attached to a chamber ring 112 connected to a chamber plate 114. The fixed disk 108, chamber ring 112, and the chamber plate 114 form a buffer chamber to allow the ambient air entering the ambient air dilution cartridge 106 to temporarily decelerate while a user is inhaling to smell. This allows air entering through the clean air inlet cartridge 104 and the ambient air dilution cartridge 106 to properly mix in the mask 102. Without such a chamber, air could potentially travel directly from the ambient environment to the nasal area of the user without first mixing with the clean, filtered air, which can result in incorrect detection readings. The chamber plate 114 includes an outlet hole 116 to receive a fitting 118 and attach the chamber plate 114 (i.e., and the fixed disk 108) to the mask 102 for mounting the varying air flow opening 113 formed by the fixed disk 108 and the pivoting disk 110 to the mask 102.

A position sensor measures the relative position of the structural members relative to each other. In this exemplary device, the position sensor includes a potentiometer having a sensor membrane 120 secured to the top surface of the fixed disk 108 that provides an output signal that varies as the position of the pivoting disk 110 changes relative to the fixed disk 108. Some embodiments include other types of position sensors.

The sensor membrane 120 has an inner sensor portion 120a and a ribbon connector portion 120b. The inner sensor portion 120a tracks the position of the pivoting disk 110 by detecting the relative position of pivoting disk 110. The ribbon connector portion 120b is connected to the display unit 107, or an alternative control unit, to transmit electrical signals regarding the detected relative position of the pivoting disk 110. The fixed disk 108 includes a recess sized to receive the sensor membrane 120 so that a top surface of the sensor membrane 120 is flush with the top surface of the fixed disk 108. In some embodiments, the fixed disk 108 does not include a recess to receive the sensor membrane 120. The inner sensor portion 120a is contacted by a feature (e.g., a wiper 122) of the pivoting disk 110 and the sensor 120 outputs a voltage based on the relative position of the wiper 122. The wiper 122 is secured in a recess of the pivoting disk 110 and moves along the sensor membrane 120 to produce a voltage based on the position of the pivoting disk 110 with respect to the fixed disk 108 can be determined. The wiper 122 is made from various suitable materials (e.g., metal). For example, the wiper 122 can be a threaded fastener secured in a threaded hole in the pivoting disk 110.

The sensor 120 is calibrated and the voltage output by the sensor 120 when the pivoting disk 110 is at various relative positions with respect to the fixed disk 108 is measured and stored as calibration data in a control unit or memory device. During use, the changing voltage output by the sensor 120 is sent to a control unit and the control unit, based on the stored calibration data, determines the relative position of the pivoting disk 110 with respect to the fixed disk 108.

A gasket 124 arranged on top of the fixed disk 108 limits air flow entering the orifice 109 from the space between the rotating disk 110 and the fixed disk 108 when the pivoting disk 110 is secured to the fixed disk 108. Air flows through the air opening 113 (see FIGS. 2A, 2D and 2E) formed by the orifices 109, 111 (i.e., not from between the disks 108, 110 and through the orifice 109) to help accurately control of the amount of ambient air flowing into the mask 102. The gasket 124 includes an inner recess 126 to allow the sensor wiper 122 to travel freely inside the gasket 124. The inner recess 126 also includes a flat region 126a that, when the gasket 124 is installed on the fixed disk 108, abuts a raised portion 128 extending upward from the fixed disk 108 to keep the gasket 124 properly oriented to the fixed disk 108 when the pivoting disk 110 rotates. A guide 130 inserted through a hole in the gasket 124 and fastened to the fixed disk 108 secures the gasket 124 to the fixed disk 108. The guide 130 also limits the rotation of the pivoting disk 110 during use. The guide 130 can be in the form of various structurally suitable elements. For example, in some implementations, the guide is a fastener (e.g., a cap screw). Other devices and techniques can be used to secure and align the gasket 124 to the fixed disk 108. Additionally, in some implementations, other types of sealing devices (e.g., O-rings) limit air flowing in the orifice 109 from the space between the fixed disk 108 and the pivoting disk 110.

The pivoting disk 110 also includes a guide slot 134 formed near an outer edge of the pivoting disk 110 over about 50% of the pivoting disk 110. When the pivoting disk 110 is mounted on the fixed disk 108, the guide 130 of the fixed disk 108 fits into the guide slot 134 so that as the pivoting disk 110 rotates atop the fixed disk 108, the guide 130 limits the rotation between a fully closed position and a fully open position.

The pivoting disk 110 is secured to the fixed disk 108 using a fastener 136 that passes through a recess 138 in the pivoting disk 110 and is secured into a recess 140 (e.g., a threaded hole) formed in the fixed disk 108. A spring 142 is arranged between the fastener 136 and the pivoting disk 110 to provide a downward force onto to pivoting disk 110 to help ensure an adequate seal between the pivoting disk 110 and the fixed disk 108.

During use, the pivoting disk 110 rotates to vary the amount of ambient air that can enter the mask 102 through the opening 113. The sensor 120 determines the relative rotational position of the pivoting disk 110 (i.e., the position of the wiper 122) with respect to the fixed disk 108. The relative position reading (i.e., the voltage output by the sensor 120) is used to determine (e.g., calculate) the ratio of ambient air entering the mask 102 to clean filtered air entering the mask 102 (i.e., the dilution to threshold ratio) when a user is wearing the mask scentometer 100 and breathing in.

Since the dilution to threshold ratio represents a flow ratio of clean filtered air to ambient air entering the mask 102, the size and shape of the opening 113 can be used to estimate the dilution to threshold ratio. Additionally, estimated dilution to threshold ratios based on the size of the opening 113 can be verified or otherwise determined by testing and calibration. For example, the dilution to threshold ratio based on the relative position of the pivoting disk 110 could be determined empirically by drawing air (e.g., by producing a flow to simulate a human inhaling) into the mask 102 while adjusting the pivoting disk 110 and measuring the flow of air through the filtered, clean air inlet filter 104 and the ambient air dilution cartridge 106. Once the relative flow rates through the filtered, clean air inlet filter 104 and the ambient air dilution cartridge 106, based on relative position of the pivoting disk 110, are determined, the dilution to threshold ratio for each relative position can be calculated.

A control unit 144 receives relative position information from the sensor 120 (i.e., a voltage output based on the position of the wiper 122), uses that relative position information to determine a corresponding dilution to threshold ratio based on the relative position, and displays that dilution to threshold ratio on the display unit 107. The user can typically read the dilution to threshold ratio at a given time while using the mask scentometer 100. The display unit 107 can be mounted on the mask 102 so that it is generally visible by a user while the user is wearing the mask 102. Alternatively, the display unit 107 can be in the form of a separate unit that is connected to the mask 102. For example, the display unit can be a separate unit that can be carried by a user and is tethered to the mask 102 or wirelessly connected to the mask 102. In some cases, the control unit 144 is built into the mask 102 and is electrically connected to the display 107.

Alternatively or additionally, as another example of a position sensor that can signal the degree of overlap between the first and second orifices, the disks (e.g., the fixed disk 108, the pivoting disk 110, or both) can include a visual scale or dial indicator to denote the relative position of the pivoting disk 110 with respect to the fixed disk 108. The scale can also include corresponding dilution to threshold ratio information for the different relative positions.

The concepts discussed above can also be implemented in other types of scentometers. For example, these concepts can be implemented in a nasal scentometer.

Figure 3A:
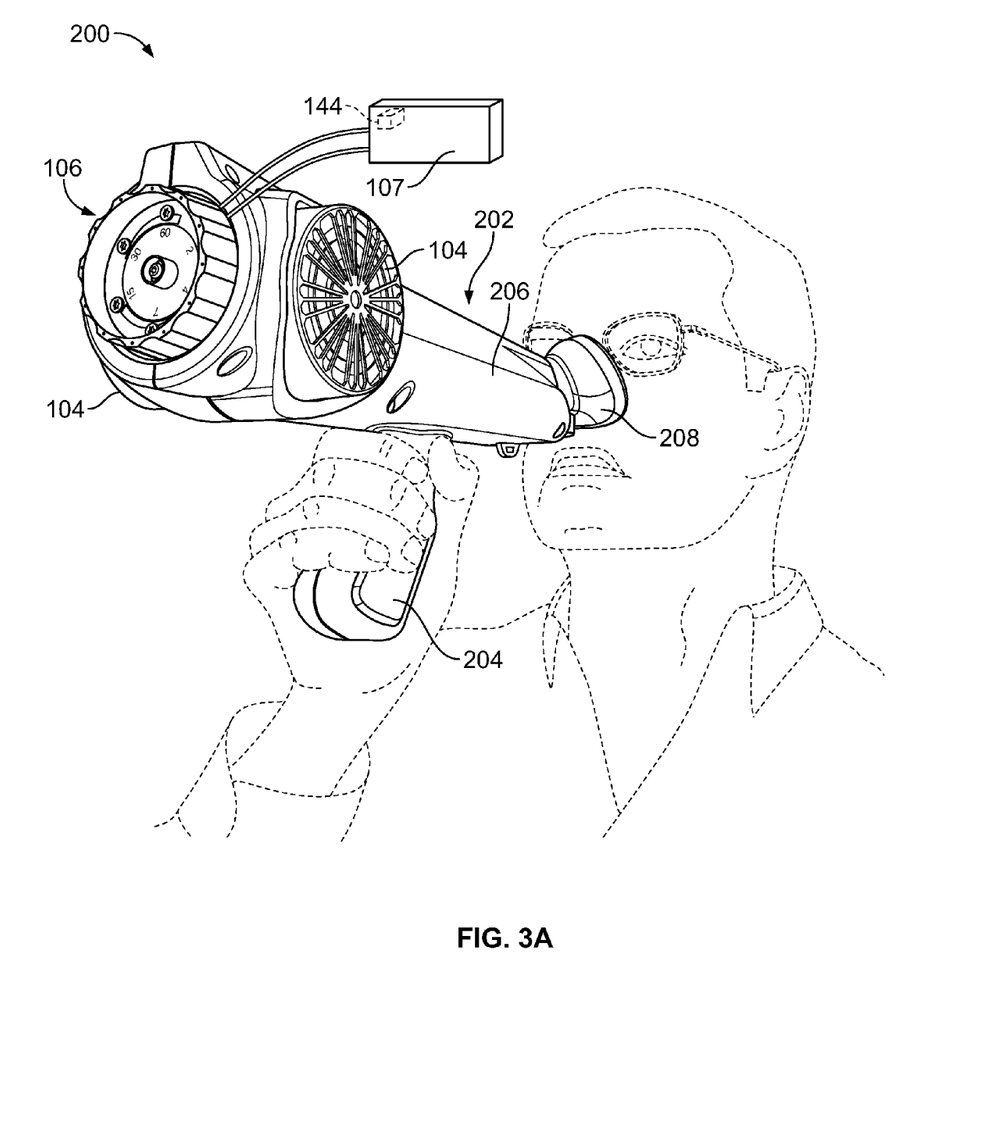
FIG. 3A is a perspective view of a nasal scentometer.

Referring to FIG. 3A, a nasal scentometer 200 includes an inhalation apparatus 202, two clean air inlet cartridges 104, an ambient air dilution cartridge 106, and a display unit 107. The clean air inlet cartridges 104 are arranged on holes on opposite sides of the inhalation apparatus 202 and the ambient air dilution cartridge 106 is arranged on a hole at a far end of the inhalation apparatus 202 to allow both filtered and ambient air to flow into and mix within the inhalation apparatus 202.

The inhalation apparatus 202 includes a handle 204 extending from a tube-like member 206 and a flexible (e.g., made of plastic or rubber) nose piece 208. The nose piece 208 is configured to sufficiently seal around a nose of the user. As shown, the inhalation apparatus 202 and nose piece 208 are configured to be gripped by a user and held securely against the face of the user during use. The tube-like member 206 serves as an air mixing chamber for filtered air to mix with ambient odorous air.

The inhalation apparatus 202 includes a pressure sensor positioned inside the inhalation apparatus 202 to measure the pressure at which a user inhales air into the inhalation apparatus 202. In some cases, certain inhalation pressures are used to generate desired flow characteristics in order to properly measure the dilution to threshold ratio. The pressure sensor can be connected to a control unit and an exterior display to indicate that greater or less inhalation pressure is desired from the user. The exterior display can be the display unit 107 for displaying the dilution to threshold ratio or, alternatively, it can be a separate display. Some embodiments do not include a pressure sensor within the inhalation apparatus.

Figure 3B:
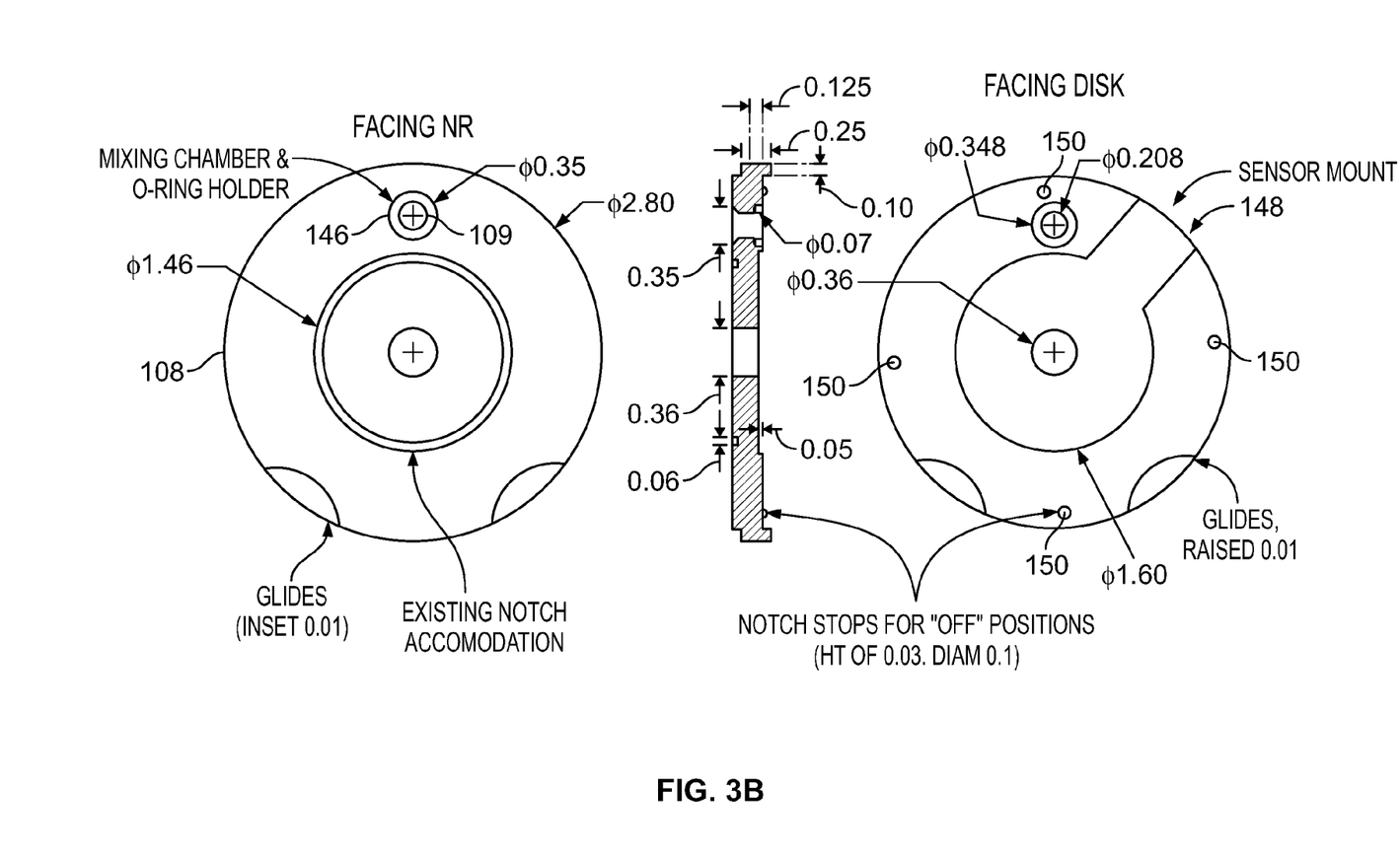
FIG. 3B is a front and back view of a fixed disk of an ambient air dilution cartridge of the nasal scentometer of FIG. 3A.
Figure 3C:
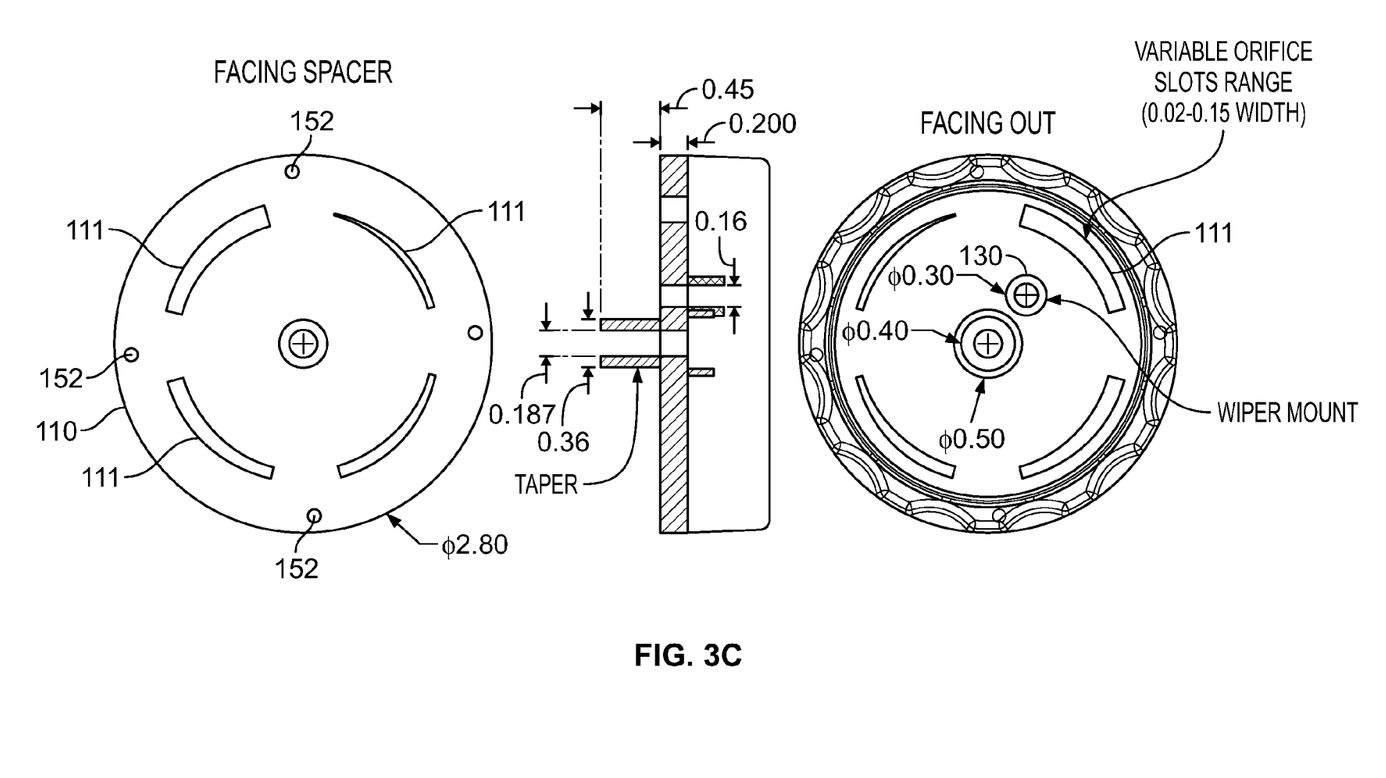
FIG. 3C is a front and back view of a pivoting disk of the ambient air dilution cartridge of the nasal scentometer of FIG. 3A.
Figure 3D:
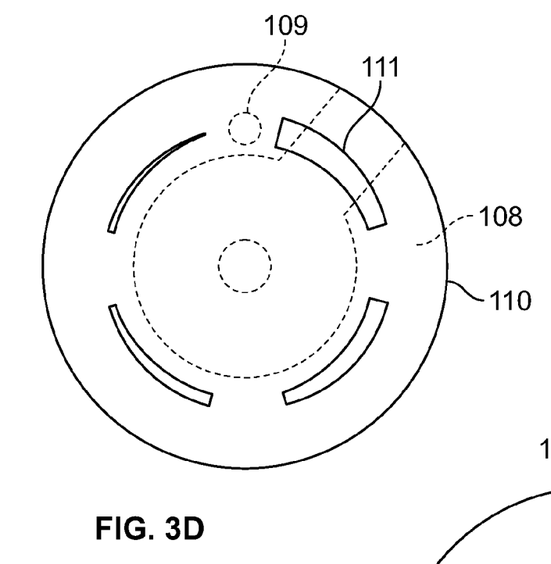
FIGS. 3D and 3E are front views of a pivoting disk rotated on a fixed disk to create an ambient air opening for the nasal scentometer of FIG. 3A.
Figure 3E:
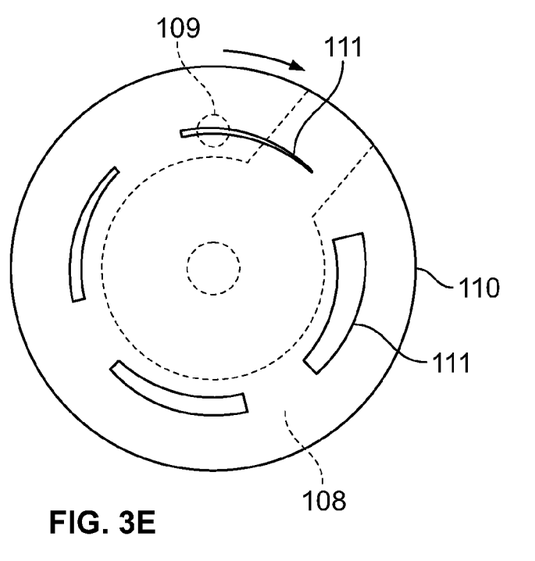
Figure 3F:
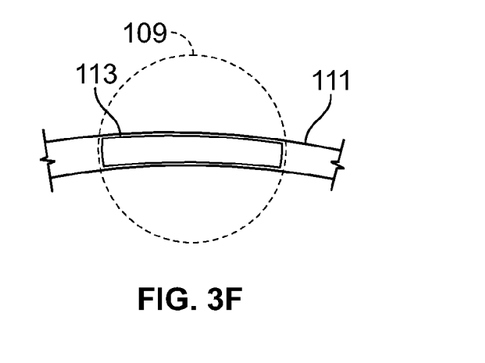
FIG. 3F is an enlarged view of the ambient air opening of FIG. 3A.

Like the mask scentometer discussed above, the ambient air dilution cartridge 106 includes two cooperating disks (e.g., a fixed disk 108 and a pivoting disk 110) that adjust the amount ambient air that can enter the inhalation apparatus 202. However, in this example, one of the disks (e.g., the fixed disk 108), referring to FIGS. 3B and 3C, includes a round orifice 109 and the pivoting disk 110 includes one or more non-uniform orifices 111 that vary in size. The non-uniform orifice 111 has a first end having a small width and smoothly extends into a second end having a width that is wider than the first end. Some embodiments include different shaped orifices. The pivoting disk 110 includes multiple orifice portions separated by regions of the disk (e.g., blanks). In some embodiments, one orifice is formed around the majority of the pivoting disk 110. Referring to FIGS. 3D-3F, when the pivoting disk 110 is pivotally secured to the fixed disk 108, the pivoting disk 110 can be rotated to align portions of the non-uniform orifices 111 with the round orifice 109. By aligning the orifices 109, 111, a variable-sized air opening 113 (shown in expanded FIG. 3F) is formed to allow ambient air to enter the inhalation apparatus 202. To provide an adequate seal between the round orifice 109 and the non-uniform orifice 111, the fixed disk 108 includes a seal member (e.g., an O-ring 146) arranged around the round orifice 109.

Referring again to FIG. 3B, the fixed disk 108 includes a sensor mount recess 148 formed to receive a potentiometer sensor 120. The sensor 120 is secured to the fixed disk 108 to detect the relative position of the pivoting disk 110 with respect to the fixed disk 108. To indicate the relative position of the pivoting disk 110 on the sensor 120, the pivoting disk 110 includes a sensor wiper 130 to move along the sensor 120 to generate a voltage output which corresponds to the relative position of the wiper 130 and therefore also of the pivoting disk 110.

The ambient air dilution cartridge 106 can also include an indexing mechanism to temporarily secure the pivoting disk in particular orientations with respect to the fixed disk. For example, referring to FIGS. 3B and 3C, the fixed disk 108 includes multiple raised portions 150 to engage indentations 152 formed along the adjoining face of the pivoting disk 110. The raised portions 150 and corresponding indentations 152 can be arranged around the disks 108, 110 at various positions to allow a user to select and maintain certain orientations or relative positions. Alternatively, other techniques or mechanisms can be used to secure the pivoting disk to the fixed disk.

The display unit 107 is used to indicate the dilution to threshold ratio based on the relative position of the pivoting disk 110 with respect to the fixed disk 108, as measured by the sensor 120. The display unit 107 includes a control unit 144 for receiving relative position signals from the sensor 120, determining a dilution to threshold ratio based on the measured position, and then displaying the dilution to threshold ratio on the display unit 107. Alternatively, the display unit 107 can be connected to an external control unit that processes the relative position signals and determines a dilution to threshold ratio. In cases where the nasal scentometer 200 includes a pressure sensor inside the inhalation apparatus 202, the pressure sensor can be connected to the control unit 144 so that the inhalation pressure can be considered when determining the dilution to threshold ratio.

The scentometers can be used, for example, in determining an odor level in areas surrounding odor producing environments (e.g., feed lots, industrial facilities, sewage plants, and other similar environments). The odor of a body of ambient air is typically quantified by determining a dilution to threshold ratio (D/T) of clean, filtered air to ambient, odorous air at which a human test subject begins to detect the odor in the ambient air.

Typically, a user will travel (e.g., in an automobile) to the area to be analyzed. While still in the automobile or in a structure (e.g., a building, an office, a job trailer, or other a similar structure), to prevent exposure to the ambient air containing the odor, the user places a mask scentometer 100 on their face and secures it using the straps. With the mask scentometer 100 secured to the face, the user rotates the pivoting disk 110 to a fully closed position where the pivoting orifice 111 does not overlap the fixed orifice 109 (i.e., no opening 113 is formed) so that no air enters the mask 102 through the ambient air dilution cartridge 106. Alternatively, if using a nasal scentometer 200, instead of securing a mask to the user's face, the nose piece 208 is held in place on the user's nose. With the ambient air dilution cartridge 106 closed, the user only breaths air that passes through the clean air inlet filter 104 and therefore has been filtered and has little to no odor from the ambient environment. Once the user is breathing only filtered air, the user can leave the automobile or building to begin analyzing the ambient air.

Once in the environment to be tested, the user slowly opens the ambient air dilution cartridge 106 (i.e., by rotating the pivoting disk 110) to allow ambient, unfiltered air to begin entering the mask 102 (or inhalation apparatus 202 when a nasal scentometer 200 is used). The user rotates the pivoting disk 110 in a slow and controlled manner in increments (e.g., small rotational distances), continuously smelling the air entering the mask 102 or the inhalation apparatus 202 in an attempt to detect an odor. The user continues to rotate the pivoting disk 110 to increase the size of the opening 113 and increase the flow of ambient odorous air entering the mask 102 or the inhalation apparatus 202. When the user detects the odor, he or she stops rotating the pivoting disk 110 and determines dilution to threshold ratio of air entering the mask 102 or inhalation apparatus 202 when the pivoting disk 110 is at that particular position. The dilution to threshold ratio can be determined from reading the display unit 107 or alternatively by reading the scale (e.g., graduations) formed on the fixed disk 108 or the pivoting disk 110.

In some cases, the user adjusts the pivoting disk 110 until he or she detects an odor in order to obtain an initial, coarse dilution to threshold ratio reading. Then, once the user knows the general range of the dilution to threshold ratio, the user will adjust the pivoting disk 110 more slowly to obtain a second, finer and more accurate dilution to threshold ratio reading.

A number of embodiments of the invention have been described. Nevertheless, it will be understood that various modifications may be made without departing from the spirit and scope of the invention. Accordingly, other embodiments are within the scope of the following claims.

What is claimed is:

1. An olfactory device comprising:
a housing having a first inlet and a second inlet;
an ambient air inlet cartridge defining a channel in fluid communication with the first inlet, the ambient air inlet cartridge comprising:
a first member having a first orifice;
a second member having a second orifice; wherein the second member is movable relative to the first member to create a continuously-variable ambient air inlet size; and
a position sensor generating at least one or more values indicating the degree of overlap between the first orifice and the second orifice; and
a controller adapted to receive the one or more values from the position sensor and to determine a dilution-to-threshold value based at least in part on one or more values.

2. The olfactory device according to claim 1, wherein the olfactory device comprises a visual scale, indicating the degree of overlap, and located on either the first member or the second member.

3. The olfactory device according to claim 1, wherein the position sensor comprises a potentiometer to detect the degree of overlap.

4. The olfactory device according to claim 3, wherein the potentiometer comprises a detection membrane secured to the first member and a position indicator secured to the second member.

5. The olfactory device according to claim 3, further comprising a display unit to display a dilution-to-threshold value.

6. The olfactory device according to claim 5, wherein the dilution-to-threshold value is an approximated air flow ratio of an amount of air entering the housing through the second inlet to an amount of air entering the housing through the first inlet.

7. The olfactory device according to claim 1, wherein when the second member is in the first position, an amount of air that can enter the housing through the ambient air inlet cartridge is greater than the amount of air that can enter the housing through the ambient air inlet cartridge when the second member is in the second position.

8. The olfactory device according to claim 1, when the second member is in the second position, the first orifice is covered by the second member and the second member limits air flow from entering the housing through the ambient air inlet cartridge.

9. The olfactory device according to claim 1, wherein the second member is a disk and the disk is rotatable relative to the first member.

10. The olfactory device according to claim 1, wherein the first and second orifices have the same general shape and size.

11. The olfactory device according to claim 1, wherein the second orifice has a first end having a first width and a second end having a second width, the second width being greater than the first end.

12. The olfactory device according to claim 1, wherein the housing comprises a face mask.

13. The olfactory device according to claim 1, wherein the housing has an outlet in fluid communication with the first and second inlets, and wherein the outlet is sized to be temporarily secured around a human nasal area.

14. An olfactory device comprising: a housing having a first inlet and a second inlet; and
an ambient air inlet cartridge defining a channel in fluid communication with the first inlet, the ambient air inlet cartridge comprising:
a first member defining a first orifice; and a second member moveable relative to the first member, the second member defining a second orifice wherein a degree of overlap between the first orifice and the second orifice controls a flow capacity of the channel,
the second member being movable relative to the first member between a first terminal end position, wherein the first and second orifices are offset from one another, and a second end position, wherein the first and second orifices are completely aligned and as the second member moves between the first terminal end position and the second terminal end position, the degree of overlap between the first orifice and the second orifice increases over a continuous range;
a position sensor generating at least on or more values indicating the degree of overlap between the first orifice and the second orifice; and
a controller to receive the one or more values from the position sensor to determine a dilution-to-threshold value based at least in part on one or more values.

15. A method of assessing odor, the method comprising:
withdrawing an amount of filtered air into a housing;
withdrawing an amount of ambient air into the housing to form a mixture with the filtered air, the amount of ambient air being less than the amount of filtered air;
determining the presence of an odor in the mixture;
in response to determining that no odor is present, increasing the amount of ambient air withdrawn into the housing, the amount of ambient air being increased through a continuous range; and
when an odor is detected, determining a ratio of the amount of filtered air to the amount of ambient air being withdrawn into the housing.

16. The method according to claim 15, wherein the determining the ratio comprises reading the ratio from a display unit.

17. The method according to claim 15, wherein the determining the ratio comprises detecting a relative position of two orifices that move relative to one another to form a compounding air flow passage to allow the ambient air to enter the housing.

18. The method according to claim 17, wherein the compounding air flow passage changes in size along a continuous range.

* * * * *

UNITED STATES PATENT AND TRADEMARK OFFICE
CERTIFICATE OF CORRECTION

PATENT NO.            : 8,826,723 B2  
APPLICATION NO.       : 13/421048  
DATED                 : September 9, 2014  
INVENTOR(S)           : Christopher G. Henry Page 1 of 1

It is certified that error appears in the above-identified patent and that said Letters Patent is hereby corrected as shown below:

On the Title Page

Column 2, First Page, Line 2 (Other Publications), please delete "Moniotiring" and insert -- Monitoring --, therefor.

In the Claims

Column 10, Line 37 (approx.) (Claim 14), please delete "on" and insert -- one --, therefor.

Signed and Sealed this
Sixteenth Day of December, 2014

Michelle K. Lee
*Deputy Director of the United States Patent and Trademark Office*